(12) United States Patent
Middlesworth et al.

(10) Patent No.: US 7,870,651 B2
(45) Date of Patent: Jan. 18, 2011

(54) ELASTICIZED SIDE MEMBERS

(75) Inventors: Jeffrey Alan Middlesworth, Wauconda, IL (US); Andrew J. Peacock, Richmond, VA (US); Matthew J. O'Sickey, Powhatan, VA (US); Stephen D. Bruce, Montpelier, VA (US)

(73) Assignee: Tredegar Film Products Corp., Richmond, VA (US)

( * ) Notice: Subject to any disclaimer, the term of this patent is extended or adjusted under 35 U.S.C. 154(b) by 703 days.

(21) Appl. No.: 11/729,146

(22) Filed: Mar. 28, 2007

(65) Prior Publication Data
US 2007/0234529 A1    Oct. 11, 2007

Related U.S. Application Data

(60) Provisional application No. 60/790,664, filed on Apr. 10, 2006.

(51) Int. Cl.
*A44B 18/00*  (2006.01)

(52) U.S. Cl. ........................................................ 24/442

(58) Field of Classification Search .................... 24/442, 24/306, 450, 452, 304, DIG. 11; 604/389, 604/391; 428/99, 100
See application file for complete search history.

(56) References Cited

U.S. PATENT DOCUMENTS

| | | | |
|---|---|---|---|
| 5,135,800 A * | 8/1992 | Nagaoka et al. | 428/216 |
| 6,255,236 B1 | 7/2001 | Cree et al. | |
| 6,692,477 B2 * | 2/2004 | Gibbs | 604/386 |
| 6,740,071 B2 * | 5/2004 | Gibbs | 604/392 |
| 6,942,651 B2 * | 9/2005 | Gibbs | 604/389 |
| 2007/0142815 A1 * | 6/2007 | Macura et al. | 604/389 |

* cited by examiner

*Primary Examiner*—James R Brittain
(74) *Attorney, Agent, or Firm*—Joseph A. Tessari

(57) ABSTRACT

The disclosure provides embodiments for elasticized members used as closures for garments, such as diapers, jacket cuffs, and similar articles, the elasticized member having an elastic body having an attachment region adapted for attachment of the elastic body to a garment and a fastener positioned on a distal portion of the elastic body, wherein the elastic body is structured to reduce curl along longitudinal edges and corners of the elastic body upon application of tension to the fastener.

18 Claims, 4 Drawing Sheets

ELASTICIZED SIDE MEMBERS

CROSS-REFERENCE TO RELATED APPLICATIONS

This application claims the benefit of U.S. Provisional Application No. 60/790,664, filed Apr. 10, 2006 entitled DIAPER SIDE TABS AND METHODS REGARDING SAME.

FIELD OF THE DISCLOSURE

The present disclosure is related to side members for use in releasably fastening an article about the wearer. More specifically, the disclosure concerns elasticized side members for use in securing articles about the waist of the wearer.

BACKGROUND OF THE DISCLOSURE

Many articles, particularly those that are worn about the waist, include a side member that permits the article to be secured about the waist of the wearer. In baby diapers, for example, it is common to provide an elastic member containing a hook-and-loop type fastener which permits the diaper to be secured to the infant or child and, if necessary, released and re-positioned or re-fastened. These elastic members are typically attached at one end to the diaper chassis and contain the hook-and-loop or adhesive tape element on the free end. A mating member for the fastener (be it hook-and-loop or adhesive) is positioned on the front portion of the diaper. In use, the diaper is positioned behind the baby and the side tabs are drawn forward and secured to the front portion of the diaper.

In the diaper field, the elasticized side members are generally classified as side tabs, side ears, or side panels. A side member is typically considered a "tab" if its width is around 60 mm or less and an "ear" if its width is greater than about 60 mm. A side "panel" is generally an integral member forming the side of the diaper and, unlike "tabs" or "ears" is not re-fastenable or re-positionable. Side panels are typically found on "pull-up" style training pants and can be formed by seaming or otherwise joining together ears located on the front and back portions of the diaper chassis.

Apart from their dimensions, side "tabs" and side "ears" also differ functionally. A side tab is generally employed on a diaper chassis having an hourglass shape—wider at the front and back and narrower in the middle (crotch) area. The enlarged chassis portions of the hourglass shape form not only the front and back of the diaper, but also the sides of the diaper and the upper portion of the leg opening when they are brought together as the diaper is applied to the baby. Thus, the function of the tab is merely to keep the enlarged portions of the hourglass chassis together.

A side ear, however, is typically used on a rectangular-shaped chassis and applied to the chassis are that forms the back of the diaper. Once the ears are attached, the diaper takes a "T-shaped" appearance, with the "ears" forming the horizontal member of the "T" shape and the rectangular chassis forming the vertical member. As the diaper is applied to the child, the ears are pulled forward and attached to the front of the diaper. The ear not only serves to keep the diaper fastened about the waist, but also will form the side of the diaper and the upper portion of the leg opening.

Furthermore, the elastic used in an ear generally has lower extension and retraction forces compared to the elastic typically employed in tabs. Generally speaking, as the size of the elastic side member increases, the forces necessary to maintain the fit of the diaper are spread across larger area. Also, the larger area means that the force necessary to extend the elastic will increase unless elastic having lower extension forces is used. The higher extension force may make it difficult to extend the side member during the diapering process or during movement of the child while wearing the diaper, compromising both fit and comfort. In addition, if the retraction forces of the elastic are too high, the diaper will fit too tightly, causing discomfort to the child and reddening or abrasion of the skin. Accordingly, it is important to maintain the balance of extension and retraction forces as the size of the elastic side member changes.

As mentioned, both ears and tabs typically employ an adhesive element or a hook-and-loop fastener to enable the diaper to be opened and closed repeatedly. The fastening element, particularly the hook-and-loop type, is a relatively expensive component for a diaper and is a significant contributor to the overall cost of the diaper. Furthermore, as the size of the fastening element increases, the forces necessary to disengage the element to open the diaper increase. If those forces get too high, the outer covering of the diaper may tear or pull apart as the diaper is opened. Thus, it is advantageous to minimize the amount of the fastening element used in the manufacture of the diaper and to use no more than is generally necessary to enable the diaper to remain secured to the child. While this is generally not a problem with side elastic members that are closely matched to the size of the fastening element, it is problematic with elastic side members that are larger in size.

For example, it would generally be considered impractical to apply a hook-and-loop fastener to the entire width of a side component that is 100 mm in width, for example. Thus, the fastener is applied only to a portion of the side elastic component. For example, the width of the hook-and-loop element may only be 30 mm, leaving 70 mm of width of the side member without any fastening element. In such a construction, when tension is applied to the elastic side component, either during the diapering process or during movement of the child, the stress is concentrated in the 30 mm area corresponding to the location having the fastening element. As a result of the uneven stresses, the portions of the elastic side member not having the fastening component tend to curl and become distorted. Apart from an unattractive appearance, the distortion in the ear may result in improper fit of the diaper, and the diaper may fall off, leak, or have other undesirable attributes.

To address these concerns, it is known to use elastic that has a higher elongation forces and/or higher retraction forces. Elastics that require higher extension forces would be less likely to curl or distort when tension is applied to the fastener. By switching to "stronger" elastic, the ear will be more resistant to distortion, but will also increase the cost of the diaper. In addition, elastics that have higher elongation/retraction forces may result a diaper that is too difficult to apply (i.e., takes too much force to extend the ear) or results in reddening of the baby's skin because the retraction forces are too high.

Thus, there is a need in the art for additional ways of making side ears that saves materials, offer less expensive solutions, and still allow for attractive and functional diaper constructions.

SUMMARY OF THE INVENTION

In one aspect, the embodiments provide elastic side elements for use in diapers and similar articles.

In another aspect, the embodiments provide elastic side elements that are shaped and constructed to promote more uniform distribution of forces when the element is placed under tension.

These and other features of the embodiments will become apparent upon a further reading of the detailed description with reference to the appended drawings.

DETAILED DESCRIPTION OF THE EMBODIMENTS

Figure 1:
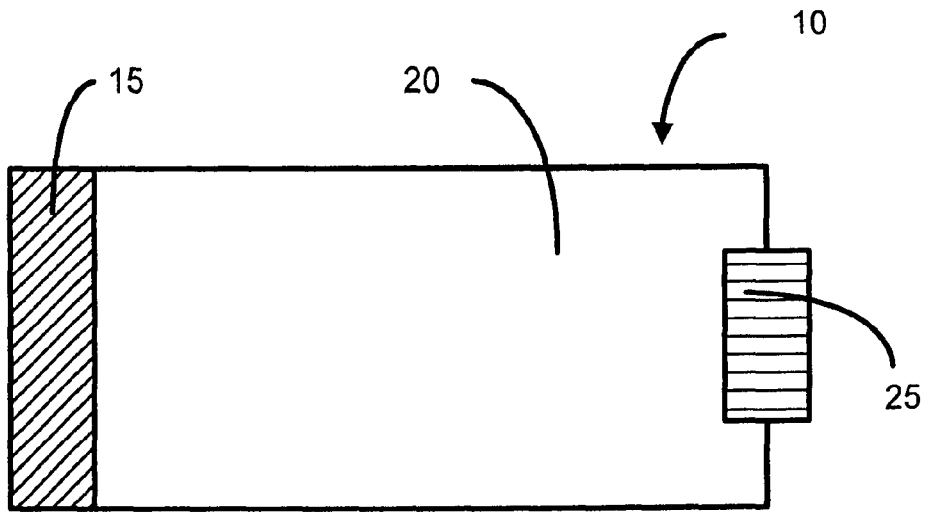
FIG. 1 is a schematic illustration of a typical diaper side tab.

FIG. 1 is a schematic illustration of a typical prior art diaper side tab 10. The tab 10 comprises a body portion 20 which has a region 15 where the tab is attached to the chassis of a diaper (not shown). The attachment of the tab 10 to the diaper is generally accomplished by one or more bonding methods, such as adhesive bonding, thermal bonding, ultrasonic bonding, stitching, etc.

On an end of the tab 10 opposite the region 15 is a fastener 25. The fastening element is typically either an adhesive tape or a hook-and-loop type fastener, such as VELCRO®, available from Velcro USA, Inc., Manchester, N.H. The diaper is typically applied while the child is on its back. Thus, it is customary for the tab 10 to be attached at region 15 to the back portion of the diaper and for the fastener 25 to be positioned for engagement with the front of the diaper. Accordingly, the front portion of the diaper will normally be constructed with a zone adapted to cooperate with the fastener 25 to maintain the diaper in a secured position about the waist of the wearer. For example, when using an adhesive tape as the fastener 25, the front of the diaper may be provided with a "landing zone" comprising a smooth release surface to engage the tape. Similarly, if a hook-and-loop type material us used as the fastener 25, it is customary to apply the hook portion to the tab 10 and to provide the front of the diaper with a mating loop surface, typically a nonwoven material.

The body portion 20 of the tab 10 is elastic; that is, it is capable of being stretched by application of a pulling force and will retract once that pulling force is removed. The elastic body 20 will typically comprise an elastic film sandwiched between two layers of a nonwoven fibrous material. It is also known to use elastic strands in lieu of an elastic film. The term "nonwoven" is used to connote a web formed from a plurality of fibers that are interlaced together, but not in any repeating pattern. Such materials are widely available from a variety of sources and are well know in the art.

Figure 2:
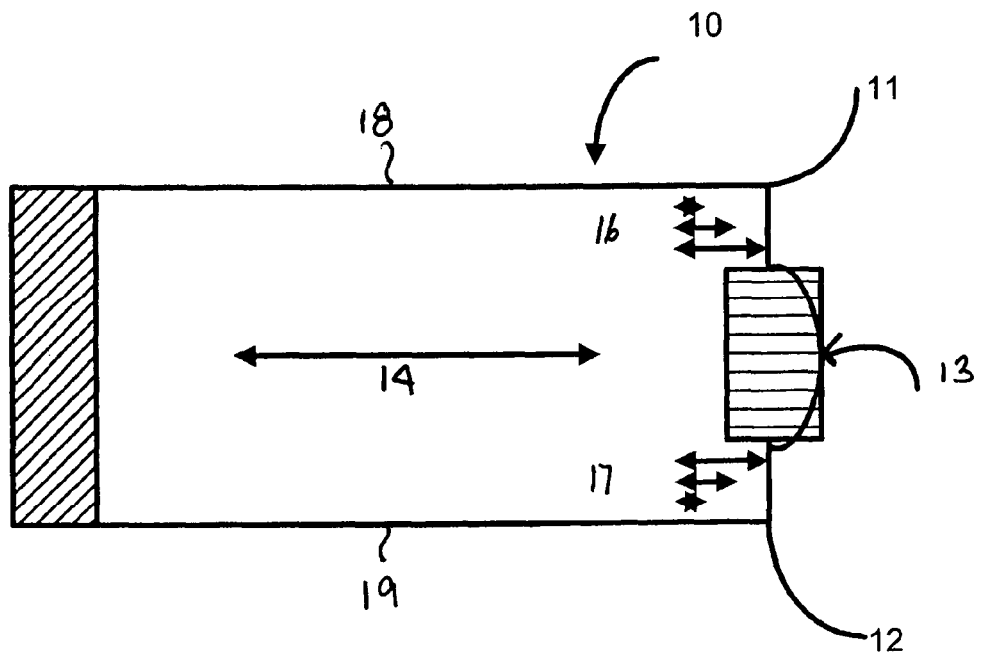
FIG. 2 is a schematic illustration of a typical diaper side tab illustrating the forces imparted to the tab.

In use, the tab 10 will typically be grasped at or near the fastening element 25 in a region generally indicated at 13 in FIG. 2. A finger lift (not shown) may be provided to facilitate grasping and pulling the tab 10. Once the tab is grasped, it will be pulled toward the front of the diaper (i.e., away from region 15 where the tab 10 is attached to the diaper) and the fastening element 25 will be engaged with the appropriate cooperating region on the front of the diaper. The pulling action against the tab will cause elastic body 20 to elongate. Once the fastener element 25 has been engaged, the elastic body 20 will attempt to retract back to its original dimensions, but is prevented from doing so by the fastener element 25. The retraction forces exerted by the elastic body 20 of tab 10 maintain the diaper around the waist of the child. The extension and retraction forces of the elastic body 20 are generally indicated in FIG. 2 by arrow 14.

As also depicted in FIG. 2, the stretch forces in the tab 20 tend to be concentrated in the area where the tab is grasped and pulled. For example, in the illustration in FIG. 2, the user is pulling on tab 10 by grasping the region 13. Such action places the maximum tension to the tab at the region 13, causing the elastic body 20 to elongate more in the longitudinal area corresponding to that region. As indicated by the series of arrows 16 and 17, the stresses in the elastic body 20 are at a minimum along the longitudinal side edges 18, 19, respectively, of the tab 10 and especially at the corners 11, 12. Between the point 13 and the longitudinal edges 18, 19, the stresses gradually decrease. Because the distribution of forces is uneven, the elastic body 20 elongates unevenly, and the edges 18, 19 and especially corners 11, 12 will curl or otherwise becoming distorted. As the width of the tab (i.e., the distance between longitudinal edges 18, 19) increases, the distortion and curling becomes more pronounced. The embodiments disclosed herein overcome this problem using a variety of techniques and constructions of the tab.

In the following description of the preferred embodiments, the term "tab" is used to reference re-fastenable or repositionable elastic elements such as those that might be used on a diaper. It is not intended to be used to denote a particular size, nor to distinguish side elements that might generally be referred to as diaper "ears." Also, while the embodiments are described with reference to side elements on a diaper, the invention is not limited to diapers. Instead, the embodiments disclosed are suitable for use in other garments or articles that utilize elastic bands, flaps or other components as part of an attachment or closure mechanism. For example, the embodiments may be used as elastic closures for hats and caps, wrist cuffs on jackets and coats, devices for retaining bed sheets or ironing board covers, and in similar applications. For ease of understanding, like reference numbers are used in the Figures to reference similar components of construction.

Figure 3:
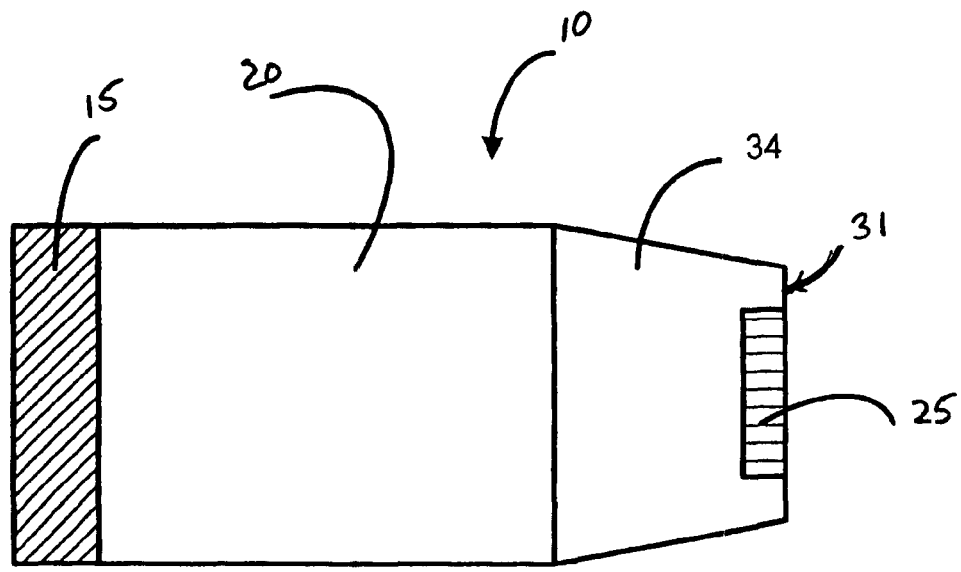
FIG. 3 is a schematic illustration of a side tab in accordance with one embodiment.

With reference to FIG. 3, the embodiment illustrated therein comprises a tab 10 having an elastic body 20. At one end of elastic body 20 is the attachment region 15 at which the tab 10 is secured to a diaper. The region 15 is preferably substantially inelastic and inextensible to provide a more secure attachment. For example, region 15 can be rendered substantially inelastic by selectively activating the elastic laminate used for body portion 20, such that region 15 is not activated. Alternatively, region 15 can be provided with a strip of film, such as polypropylene film, to render it inelastic as taught in U.S. Pat. No. 6,255,236, the disclosure of which is incorporated herein by reference. The term "substantially inelastic and inextensible" is used to indicate that the region need not be totally incapable of extension or completely devoid of elasticity, but those two properties should be minimized for the best performance.

At the end of body 20 opposite the attachment region 15 is a tapered region 34. Tapered region 34 is widest at its point of attachment to elastic body 20 and tapers toward the distal edge 31 of the tab 10. A fastener 25 is located at the distal edge 31 of tapered region 34. It should be understood that the fastener may also be positioned on the underside (as viewed in the Figures) of the elastic body 20 and may be set back from the distal edge 31, if desired.

In the embodiment of FIG. 3, the tapered region 34 is not elastic or extensible. Preferably, the tapered region 34 is prepared from a relatively rigid polyolefin film or a rigid nonwoven and may even be stiffened in accordance with U.S. Pat. No. 6,255,236. The tapered region 34 provides the tab 10 with a pleasing overall aesthetic appearance and will transfer the pulling forces to the elastic body along the entire point of attachment between the tapered region 34 and the elastic body 20. Accordingly, the stress exerted on the elastic body 20 when tension is applied will be relatively equally dispersed and the tab 10 will retain its shape and function.

Figure 4:
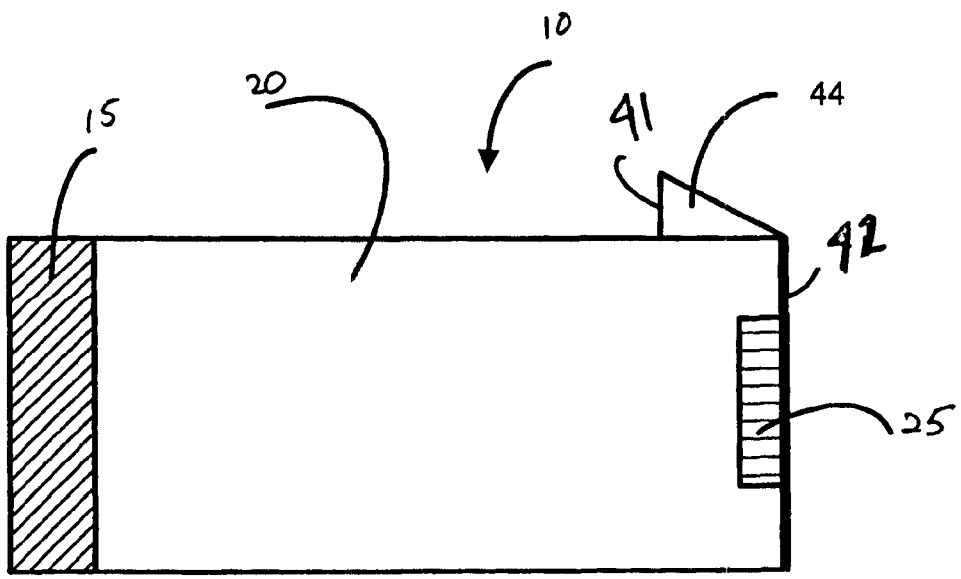
FIG. 4 is a schematic illustration of a side tab in accordance with one embodiment.

FIG. 4 shows another embodiment of a tab in accordance with the invention. In this embodiment, tab 10 comprises an elastic body 20 having at one end an attachment region 15 for attaching the tab 10 to a diaper chassis, for example. Preferably the attachment region is not elasticized or is otherwise rendered inelastic as in the previous embodiment. In this embodiment, the distal edge 41 of the elastic body 20 is folded back toward the attachment region 15, forming a flap 44 and a fold edge 42. A fastener 25 is attached to the fold edge 42. By folding over the distal edge of the elastic body 20, a thicker portion is created by the flap 44 and the fold edge 42. The thicker fold edge 42 is better able to resist the curling and distortion that might otherwise occur when tension is applied to the tab 10. In effect, this embodiment acts like heavier elastic in terms of resisting distortion, but without the increased concerns over excessive extension or retraction forces. It should be understood that flap 44 is shown loose in FIG. 4, but in most instances it will be desirable to secure that edge to the elastic body 20. Securing flap 44 to elastic body 20 will even further improve the performance of the tab 10 in resisting distortion and curling. Thickening the fold edge 42 of the elastic body 20, it will be understood, can be achieved in other ways, such as by adding a separate piece of elastic or inelastic material to the distal edge, thus obtaining the same effect, but without folding the edge over.

Figure 5:
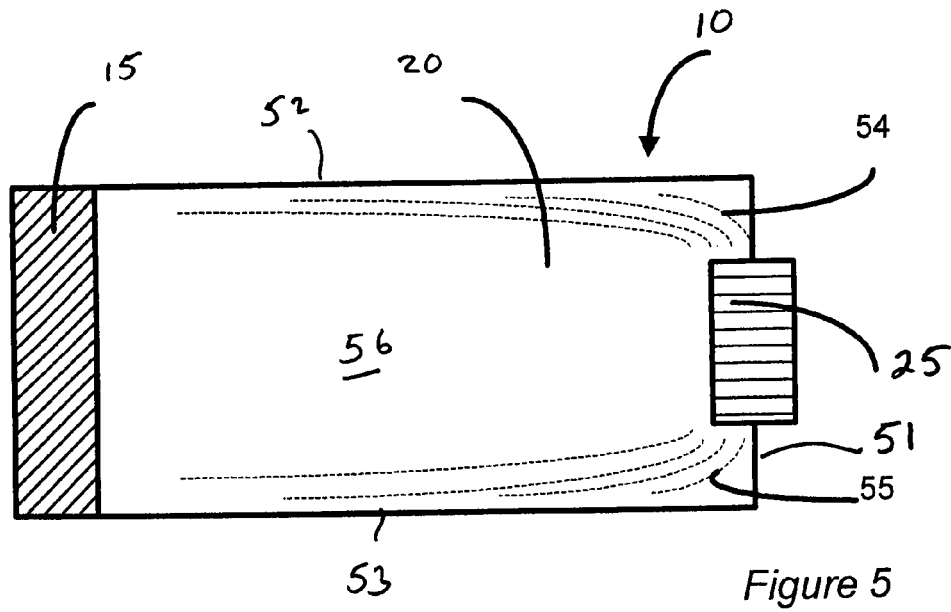
FIG. 5 is a schematic illustration of a side tab in accordance with one embodiment.

FIG. 5 illustrates yet another embodiment of a tab in accordance with the invention. In this embodiment, the tab 10 comprises an elastic body 20 having an attachment region 15 at one end thereof. Attachment region 15, as noted above, is preferably inelastic and/or inextensible. The distal edge 51 of elastic body 20 is provided with a fastener 25. As seen in FIG. 5, the elastic body 20 is provided with a series of slits positioned generally along the longitudinal edges 52, 53 of the elastic body 20 and in the corners where the longitudinal edges 52, 53 meet the distal edge 51. Upon application of tension to tab 10, the stresses in elastic body 20 will cause the slits 54, 55 to flex and open. This movement of the slits, in turn, will facilitate the orientation of stress in the elastic body 20 such that the stress is directed toward the central portion 56 of the elastic body 20. By re-directing the forces away from the longitudinal edges and corners, the tendency of the tab to curl or distort under tension is reduced.

It is understood that the number, size, shape and position of the slits will be determined depending upon the particular construction of the tab, including the material used for the elastic body 20, the size of the tab, and the specific application of the tab. Of course, slitting the tab can cause weakening and may lead to failure of the tab. Accordingly, care should be taken in locating an orienting the slits to reduce the distortion effects, but not weaken the tab to a point where it will fail in normal use. In general, slits oriented perpendicular to the direction of stretch would be most problematic in terms or tearing and thus should be avoided.

Figure 6:
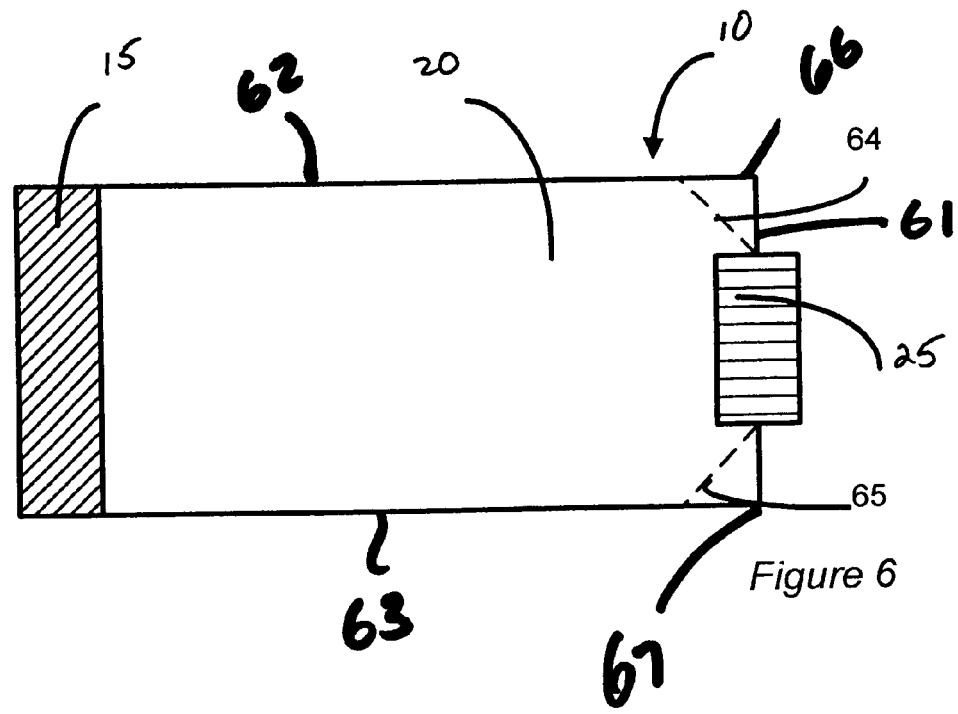
FIG. 6 is a schematic illustration of a side tab in accordance with one embodiment.

Another embodiment of a tab in accordance with the invention is shown in FIG. 6. The tab 10 comprises an elastic body 20 having an attachment region 15 at one end and a fastener 25 at the distal end 61. In the embodiment of FIG. 6, the regions on either side of fastener 25 are provided with score lines 64, 65. In the embodiment shown, the score lines 64, 65 are oriented on an angle of approximately 45°, starting at the distal edge 61 where it meets the fastener 25 and orienting outward toward the lateral edges 62, 63 and back toward attachment region 15.

The score lines 64, 65 can be made by heat to fuse the material or can be slits. The score lines provide fold lines such that, as tension is applied to the elastic body 20 by pulling on fastener 25, the corner regions 66, 67 of elastic body 20 will fold over at score lines 64, 65. The forces from the applied tension will then be transmitted along the score lines 64, 65 to the full width of the elastic body 20, similar to that mentioned in the embodiment of FIG. 3. By concentrating the stress rearward (toward the attachment region) and outward, the elastic body 20 elongates more uniformly, thus reducing or eliminating the curl. It is preferable for the corner regions 66, 67 to fold inward for a cleaner, trapezoidal-like appearance. In this embodiment, it may be preferable to reinforce or stiffen the corner regions 66, 67, such as by thermal bonding to facilitate orderly folding of the elastic body at score lines 64, 65.

While two, somewhat symmetrical score lines are illustrated, it will be appreciated that the same results can be achieved by off-setting the fastener from the central area and then scoring the larger corner area only.

Figure 7:
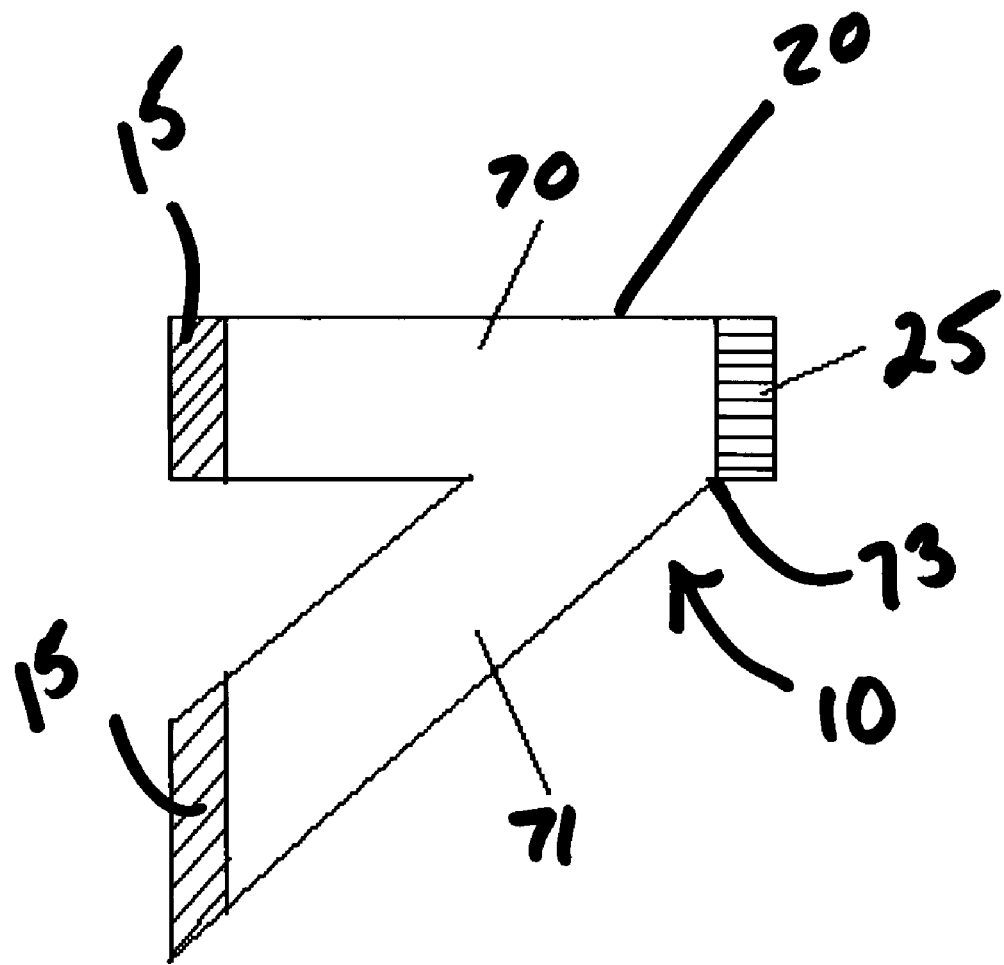
FIG. 7 is a schematic illustration of a side tab in accordance with one embodiment.

FIG. 7 shows yet another embodiment of a tab in accordance with the invention. In the embodiment shown, the tab 10 comprises an elastic body 20. As seen, elastic body 20 is a v-shaped member having elastic legs 70, 71 disposed at an angle to one another. Each of legs 70, 71 has an attachment region 15 for attachment to the diaper, for example. Fastener 25 is located at the distal end 73 of elastic body 20, which end 73 is also the apex of the legs 70, 71.

In this embodiment, the elastic forces required to provide proper fit a provided by the two elastic legs 70, 71. Thus, the width of each leg 70, 71 can be narrower than would otherwise be required when using a single elastic body. Because the leg is narrower, it is cost effective to provide a fastener along the entire width, or nearly along the entire width of the leg 70. Thus, in this embodiment, tension applied to fastener 25 is transferred primarily along leg 70 and across all or most of its width, thus improving the distribution of forces and reducing curl and distortion. Leg 71 also takes up some of the tension forces, which are also transmitted across all of most of the width of the leg 71, resulting in reduced curl and distortion.

In each of the embodiments described herein, the elastic body must comprise some type of elastic engine (i.e., a material that will provide the requisite stretch and recovery properties. Generally, the elastic engine will be either an elastic film or elastic strands. However, in lieu of a film or strand, the elastic engine can comprise elastic nonwoven, elastic adhesive, elastic scrim, or any other suitable material that will provide the requisite stretch and recovery properties.

Elastic films are known in the art and may comprise monolayer or multi-layer films. For example, the elastomeric resins used may be selected from natural and synthetic rubbers including isoprenes, styrene block copolymers (e.g., styrene/isoprene/styrene (SIS), styrene/butadiene/styrene (SBS), or styrene/ethylene-butadiene/styrene (SEBS) block copolymers) olefinic elastomers, polyetheresters, polyurethanes, etc.

Monolayer elastic films are not generally preferred for use alone because the elastomeric resins tend to make films that are tacky or sticky. Not only is this problematic in incorporating the film into a garment, but it also from the comfort of the user, particularly when the film will be used in an application involving direct skin contact. Accordingly, it is generally preferred to use multilayer films if the film is to be used by itself. Such films are also known in the art and generally comprise an elastomeric core and one or more less elastic skin layers disposed on at least one side (and usually both sides) of the core layer. Typically, the skin layers are made from a less elastic material, such as a polyolefin and, preferably, a low density polyethylene. Metallocene catalyzed polyethylene is particularly useful, alone or blended with other low density polyethylenes. Multilayer films can be prepared by coextrusion processes or extrusion lamination or extrusion coating, for example, all of which are known in the art.

Whether used in monolayer or multilayer form, it is preferable to cover the elastic material with at least one, and preferably two nonwoven layers, one on either surface of the film, to form an elastic laminate. The nonwoven materials provide softness and comfort in many applications, particularly diapers and the like. It is understood however that the use of nonwovens is not particularly preferred when direct skin contact will not be involved. The term nonwoven web is used to connote a web comprised of a plurality of fibers that are interleaved and intertwined, but with not in any repeating pattern. Generally, nonwoven webs are comprised of polyolefin fibers, such as polyethylene or polypropylene, or a bi-component fiber which is a polypropylene core surrounded by a polyethylene sheath. The nonwoven web can be prepared by spunbonding, hydro-entangling, carding, meltblowing or other known processes.

The nonwoven webs may be bonded to the elastic material by any known process, such as adhesive bonding, thermal bonding, ultrasonic bonding, or vacuum lamination, for example. In some embodiments, it may be desired for the elastic body to be breathable. In such instances, a vacuum formed elastic laminate may be used to advantage, or the elastic laminate can be apertured using hot pins, needle punching, or by using a particulate filled elastomeric resin and then stretching the resulting film, as is known in the art.

Although the present invention has been described with respect to various specific embodiments, various modifications will be apparent from the present disclosure and are intended to be within the scope of the following claims.

We claim:

1. An elasticized member for use as a closure for a garment, comprising an elastic body having an attachment region adapted for attachment of the elastic body to a garment and a fastener positioned on a distal portion of the elastic body, the elastic body further comprises means for reducing curl along longitudinal edges and corners of the elastic body upon application of tension to the fastener, wherein the means for reducing curl comprises a substantially inelastic and inextensible member attached to the distal portion of the elastic body and wherein said fastener is attached to a distal edge of said substantially inelastic and inextensible member.

2. The elasticized member of claim 1, wherein said substantially inelastic and inextensible member is trapezoid shaped and is widest at the point of attachment to said elastic body.

3. The elasticized member of claim 1, wherein said substantially inelastic and inextensible member comprises a stiffened section of said elastic body.

4. The elasticized member of claim 1, wherein said attachment region is substantially inelastic and inextensible.

5. The elasticized member of claim 4, wherein said attachment region comprises a stiffened section of the elastic body.

6. The elasticized member of claim 1, wherein the elastic body comprises an elastic engine selected from the group consisting of elastic films, elastic strands, elastic scrim, elastomeric adhesives, elastic nonwoven webs and combinations thereof.

7. The elasticized member of claim 6, wherein said elastic body further comprises at least one nonwoven web bonded to said elastic engine.

8. The elasticized member of claim 7, wherein said elastic engine comprises a coextruded elastomeric film positioned between and bonded to a nonwoven web on each surface thereof.

9. The elasticized member of claim 7, wherein said elastic body comprises a vacuum formed elastic laminate.

10. The elasticized member of claim 1, wherein said elastic body is breathable.

11. The elasticized member of claim 10, wherein said elastic body is apertured.

12. The elasticized member of claim 1, wherein said fastener is selected from the group consisting of hook-and-loop fasteners and adhesive tape fasteners.

13. An elasticized member for use as a closure for a garment, comprising an elastic body having an attachment region adapted for attachment of the elastic body to a garment and a fastener positioned on a distal portion of the elastic body, the elastic body further comprises means for reducing curl along longitudinal edges and corners of the elastic body upon application of tension to the fastener, wherein said means for reducing curl comprises the distal edge of the elastic body folded upon the elastic body to provide a folded edge, and wherein said fastener is attached to said folded edge.

14. The elasticized member of claim 13, wherein the distal edge of the elastic body is attached to the elastic body after being folded.

15. An elasticized member for use as a closure for a garment comprising an elastic body having an attachment region adapted for attachment of the elastic body to a garment and a fastener positioned on a distal portion of the elastic body, the elastic body further comprises means for reducing curl along longitudinal edges and corners of the elastic body upon application of tension to the fastener, wherein the means for reducing curl comprises a plurality of slits positioned generally along longitudinal edges of the elastic body and at corners in the distal region.

16. An elasticized member for use as a closure for a garment, comprising an elastic body having an attachment region adapted for attachment of the elastic body to a garment and a fastener positioned on a distal portion of the elastic body, the elastic body further comprises means for reducing curl along longitudinal edges and corners of the elastic body upon application of tension to the fastener, wherein the means for reducing curl comprises score lines extending from a location where said fastener is attached to the elastic body toward longitudinal edges of said elastic body, said score lines defining pre-determined fold areas of the elastic body upon application of tension to the fastener.

17. The elasticized member of claim 16, wherein the distal region defined by the score lines is stiffened.

18. An elasticized member for use as a closure for a garment, comprising an elastic body having an attachment region adapted for attachment of the elastic body to a garment and a fastener positioned on a distal portion of the elastic body, the elastic body further comprises means for reducing curl along longitudinal edges and corners of the elastic body upon application of tension to the fastener, wherein said elastic body comprises a v-shaped member, wherein the apex of the v-shaped comprises the distal region and wherein the v-shaped elastic body comprises said means for reducing curl.

* * * * *